(12) United States Patent
Anderson (10) Patent No.: US 6,456,942 B1
(45) Date of Patent: Sep. 24, 2002

(54) NETWORK INFRASTRUCTURE FOR CUSTOM MICROARRAY SYNTHESIS AND ANALYSIS

(75) Inventor: Brooke P. Anderson, Millbrae, CA (US)

(73) Assignee: Combimatrix Corporation, Burlingame, CA (US)

( * ) Notice: Subject to any disclaimer, the term of this patent is extended or adjusted under 35 U.S.C. 154(b) by 0 days.

(21) Appl. No.: 09/490,565

(22) Filed: Jan. 25, 2000

Related U.S. Application Data (60) Provisional application No. 60/116,954, filed on Jan. 25, 1998.

(51) Int. Cl.[7] ............................ G01N 33/48; G06F 19/00
(52) U.S. Cl. .................................. 702/19; 436/8; 435/6; 702/22
(58) Field of Search ............................. 702/19, 20, 21, 702/22; 205/122, 157, 162; 436/518, 8; 435/6; 422/50, 68.1

(56) References Cited

U.S. PATENT DOCUMENTS

| | | | | | |
|---|---|---|---|---|---|
| 5,653,939 | A | * | 8/1997 | Hollis et al. ................. | 204/456 |
| 5,846,708 | A | * | 12/1998 | Hollis et al. ................. | 257/253 |
| 6,203,987 | B1 | * | 3/2001 | Friend et al. .................. | 435/6 |
| 6,324,479 | B1 | * | 11/2001 | Friend et al. .................. | 435/6 |
| 6,351,712 | B1 | * | 2/2002 | Stoughton et al. .............. | 435/6 |

* cited by examiner

*Primary Examiner*—Kamini Shah
(74) *Attorney, Agent, or Firm*—Albert P. Halluin; Adam K. Whiting; Howrey, Simon, Arnold & White, LLP (57) ABSTRACT

The present invention provides methods for interfacing computer technology with biological and chemical processing and synthesis equipment. In preferred embodiments, the present invention features methods for the computer to interface with equipment useful for biological and chemical processing and synthesis in a remote manner.

1 Claim, 7 Drawing Sheets

NETWORK INFRASTRUCTURE FOR CUSTOM MICROARRAY SYNTHESIS AND ANALYSIS

The present application claims priority to U.S. Provisional Application Serial No. 60/116,954 filed Jan. 25, 1998.

FIELD OF THE INVENTION

The present invention is in the field of biological and chemical synthesis and processing. The present invention relates to methods for control of and display from devices for biological and chemical processing.

BACKGROUND OF THE INVENTION

Advances are continually emerging in the field of biological and chemical processing and synthesis equipment. Many novel and improved arrays or "gene chips" are being developed providing rapid methods for synthesizing chemical and biological materials. Examples of such technologies include those described by Pirrung et al., U.S. Pat. No. 5,143,854, those described by Southern in WO 93/22480, those described by Heller in WO 95/12808, those described in U.S. Pat. No. 5,849,486, those described in U.S. Pat. No. 5,632,957, those described in U.S. Pat. No. 5,605,662 and those described by Montgomery in WO 98/01221. The disclosure of the foregoing are herein incorporated by reference in their entirety. Methods for synthesizing chemical and biological materials may employ, for example, photolithographic techniques or electrochemical techniques. There are many pieces of biological and chemical synthesis and processing equipment that may be or are controlled with a computer interface. Increasingly, computer interface with chemical synthesis or screening is providing opportunities to synthesize large numbers of chemicals rapidly and evaluate ever larger amounts of information from biological systems.

Means for interfacing computer technology with biological and chemical processing and synthesis are only beginning to emerge. It would be useful for the computer to interface with equipment useful for biological and chemical processing and synthesis in a remote manner. An interface that runs over a network or combination of networks (the Internet, a company's own internal network, etc.), allowing the user to control the equipment remotely while maintaining a full graphical display, updated in real time or near real time may be produced.

SUMMARY OF THE INVENTION

In one aspect, the present invention provides methods for interfacing computer technology with biological and chemical processing and synthesis equipment. In preferred embodiments, the present invention features methods for the computer to interface with equipment useful for biological and chemical processing and synthesis in a remote manner. Preferably, the methods of the present invention interface so as to run over a network or combination of networks such as the Internet, an internal network such as a company's own internal network, etc. thereby allowing the user to control the equipment remotely while maintaining a graphic display, updated in real time or near real time. Preferably, the methods of the present invention are used in conjunction with solid phase arrays that employ photolithographic or electrochemical methods for synthesis of chemical or biological materials. Particularly preferred embodiments of the present invention are used in conjunction with solid or porous arrays that employ electrochemical methods for synthesis of chemical or biological materials.

In a second aspect, the present invention features a system for controlling and/or monitoring equipment for synthesizing or processing biological or chemical materials from a remote location. Such a system comprises a computer terminal remote from the equipment itself, software designed to monitor or control such equipment, and a communication means between the active part of such equipment and the computer terminal. Such a system preferably communicates between the computer terminal and the subject equipment via the internet or an internal intranet. Those skilled in the art readily understand that the software useful in such a system is highly specific depending upon the equipment itself and the parameter and conditions that need to be controlled or monitored to effect the desired processing or synthesis. As used herein, the term "remote" means not adjacent to. In effect, term is used to denote that the computer terminal for effecting and monitoring the equipment may be located in the same vicinity as or in a completely location from the equipment. The present invention effectively allows the artisan to process or synthesize biological or chemical materials using appropriate equipment in a location that is removed from the equipment itself. Moreover, the present invention allows the artisan to control or monitor more than one or a plurality of pieces of equipment from such a remote location.

The present invention may be applied in, but is not limited to, the fields of chemical or biological synthesis such as the preparation of peptide, oligomer, polymer, oligosaccharide, nucleic acid, ribonucleic acid, porphyrin, and drug congeners. In particular, the present invention may be used in conjunction with methods to create sources of chemical diversity for use in screening for biological activity, for example, for use in the rapidly developing field of combinatorial chemistry. The methods of the present invention are especially applicable to such equipment as DNA synthesizers. Such DNA synthesizers may be controlled remotely according to the methods of the present invention thereby providing a graphic readout on progress and current status and controllable over a network.

The present invention is particularly applicable to methods of electrochemical solid phase synthesis such as those described by Montgomery in WO 98/01221, the disclosure of which is herein incorporated by reference in its entirety. The present invention provides methods for remote computer control of solid phase arrays upon which chemical synthesis is performed.

BRIEF DESCRIPTION OF THE DRAWINGS

FIG. 4 represents what is displayed during DNA synthesis from a computer interface program designed according to the present invention. Display features include the state of the chip (as represented in the graphical box labeled "chip state"), the state of valves in the synthesizer, display of the chamber number in which the DNA is being synthesized, the cycle number, i.e. the cycle of DNA that the synthesis is on performing, the parameter files being used to set the parameters used in synthesis, the sequence file specifies the sequence being built, the chemical step that the machine is on (e.g. the "E-chem deblock step"), the subtask of that chemical step that the machine is on (e.g., that it is finished with the washing), the voltage and current settings of the leads, time left in the synthesis, and total time the synthesis is to run. There are various ways that a user can interact with the processing equipment through the interface. There is a "pause synthesis" button for pausing the synthesis (say, if more reagents needed to be added or for some other reason), and there is a "graceful stop" box. When the "graceful stop" box is checked, the synthesis ends at the next full cycle but before the end of all cycles, allowing the operator to remove the chip before the end of the full synthesis but at a point where the DNA chain is complete up to that point.

DETAILED DESCRIPTION OF THE INVENTION

The present invention provides methods for interfacing computer technology with biological and chemical processing and synthesis equipment. In preferred embodiments, the present invention features methods for the computer to interface with equipment useful for biological and chemical processing and synthesis in a remote manner. Preferably, the methods of the present invention interface so as to run over a network or combination of networks such as the Internet, an internal network such as a company's own internal network, etc. thereby allowing the user to control the equipment remotely and yet still have a full graphical display, updated in real time or near real time.

The methods of the present invention are especially applicable to such equipment as DNA synthesizers though they may also be applied to polypeptide synthesizers, small-molecule synthesizers, and in general to equipment useful for generating different materials or chemicals at different sites in an array of sites. The present invention is particularly applicable to methods of electrochemical solid phase synthesis such as those described by Montgomery in WO 98/01221, the disclosure of which is herein incorporated by reference in its entirety. The present invention provides method for remote computer control of solid phase arrays upon which chemical synthesis is performed.

Electrochemically based synthesis and processing equipment typically features a solid phase array containing a plurality of electrode sites. Each electrode site typically comprises an electrode, a device for applying an electrical stimulus to the electrode and a memory device coupled to the device for applying an electrical stimulus. The memory device typically receives and stores a signal that transmits the magnitude of the electrical stimulus to be applied to the electrode. Moreover, the memory device typically controls the on and off function of the electrode. Such equipment provides for the delivery of an electrical current at selective sites in biological or chemical solutions.

Figure 1:
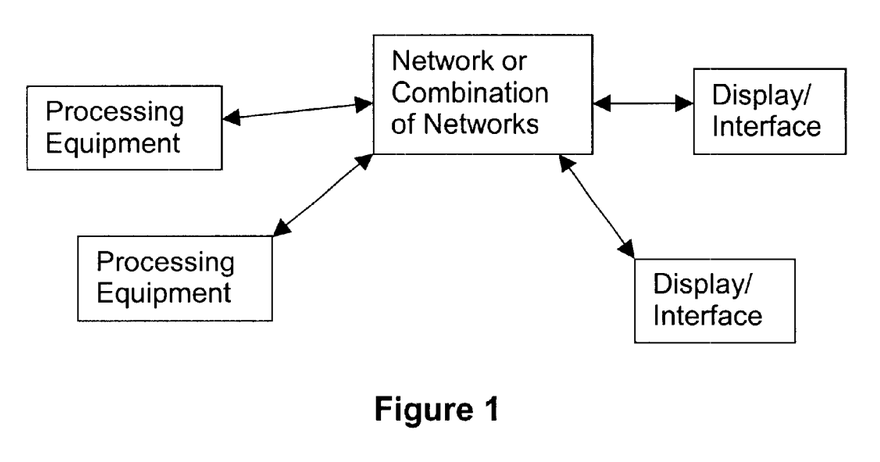
FIG. 1 demonstrates a schematic representation of the present invention whereby a network or combination of networks interfaces between a computer control and a chemical or biological synthesis or processing equipment.
Figure 2:
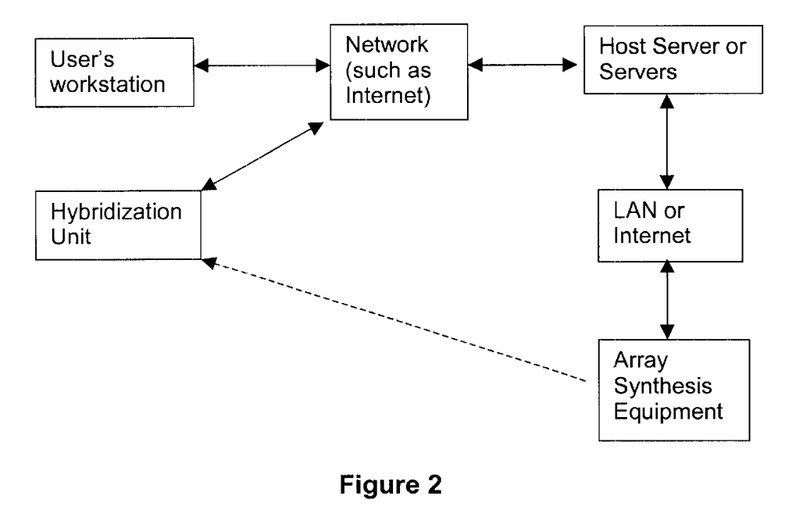
FIG. 2 represents a particular embodiment of the present invention whereby a remote workstation is linked via the Internet to an internal server or intranet which is in turn linked (preferably by the internet or an intranet) to chemical or biological synthesis equipment. Here, a user submits a list of target sequences of interest through a network server; the server designs a set of probes to capture the target sequences and submit that list of probes to the synthesizer; the synthesizer builds the probes on the surface of an array; the chip is shipped to the user; the user performs a hybridization experiment on the chip in a unit that reads the results of hybridization; the hybridization/reader unit submits the results back to a server, which further processes and formats the results; the server submits the final interpreted results back to the user through the network.

Such equipment as DNA synthesizers may be controlled remotely in this way, providing a graphical readout on progress and current status and controllable over a network. FIG. 1 demonstrates the interrelatedness of the computer interfacing with the synthesis or processing equipment. FIGS. 2–6 provide screen shots of an exemplary user interfaces for controlling and examining the status of DNA-synthesis equipment, chip-manipulation equipment, etc. Such interfaces and displays may run on a computer located remotely from the processing equipment thereby providing great advantage for the operator.

Many pieces of laboratory equipment lack "time left" displays despite the fact that they take a long time to complete their tasks. As an example, it is useful to have such equipment as DNA synthesizers show the user a readout of the time left until the synthesis is complete. We have designed a DNA-array synthesizer having such a display updated every few seconds as the synthesis is running (although the update time could be more or less than that) showing how much time remains until the process is complete. That way the operator doesn't have to keep checking or estimate the time and set a stopwatch.

Such a display demonstrates the state of the array graphically. Such contrast as colors may represent different states per site (although it could be black and white or done with characters). This feature is an important part of allowing the operator to keep tabs on the progress of the array being synthesized.

Such a display may also graphically show valve states on the fluidics portion of the machine, may provide status indicators (could be colors, black and white, words or characters) on which chemical process the machine is performing and which sub process is running.

Such a display may also have buttons for pausing the process. Pauses may be very useful in a variety of situations, including allowing the operator to replenish supplies on the machine or adjust something and for telling the machine to stop at the next "convenient" point. We call that button the "graceful stop" button.

Figure 3:
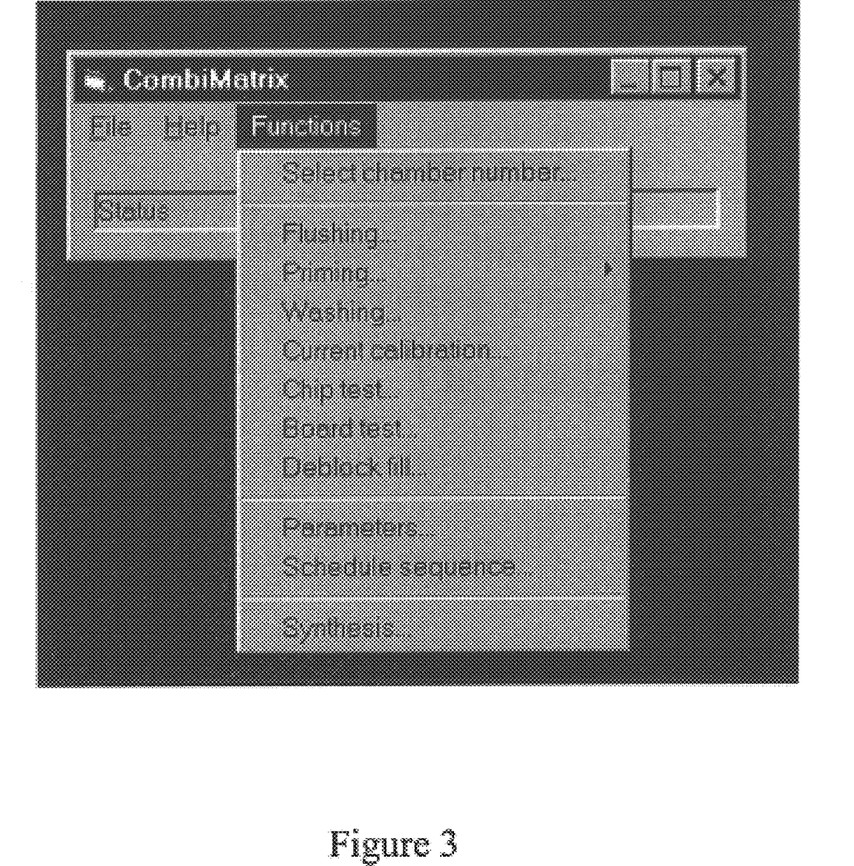
FIG. 3 demonstrates various functions that an operator can select from a computer interface program designed according to the present invention, including setting a chamber number for synthesis, flushing out a DNA synthesizer's tubing, priming the synthesizer, washing out the synthesizer's tubing, calibration of electrical current measurement, testing a gene chip, testing the interface board, filling the chamber with deblock solution, setting parameters used in synthesis, scheduling DNA sequences to build, and starting the DNA synthesis.

Preferred embodiments of the present invention feature a computer remotely in interface with a solid phase array or "gene chip" for chemical synthesis. FIG. 1 demonstrates such an interrelated arrangement. In FIG. 3, one can see various functions that an operator can select, including setting a chamber number for synthesis, flushing out the DNA synthesizer's tubing, priming the synthesizer, washing out the synthesizer's tubing, calibrating electrical current measurement, testing the chip, testing the interface board, filling the chamber with deblock solution, setting parameters used in synthesis, scheduling DNA sequences to build, and starting the DNA synthesis.

Figure 4:
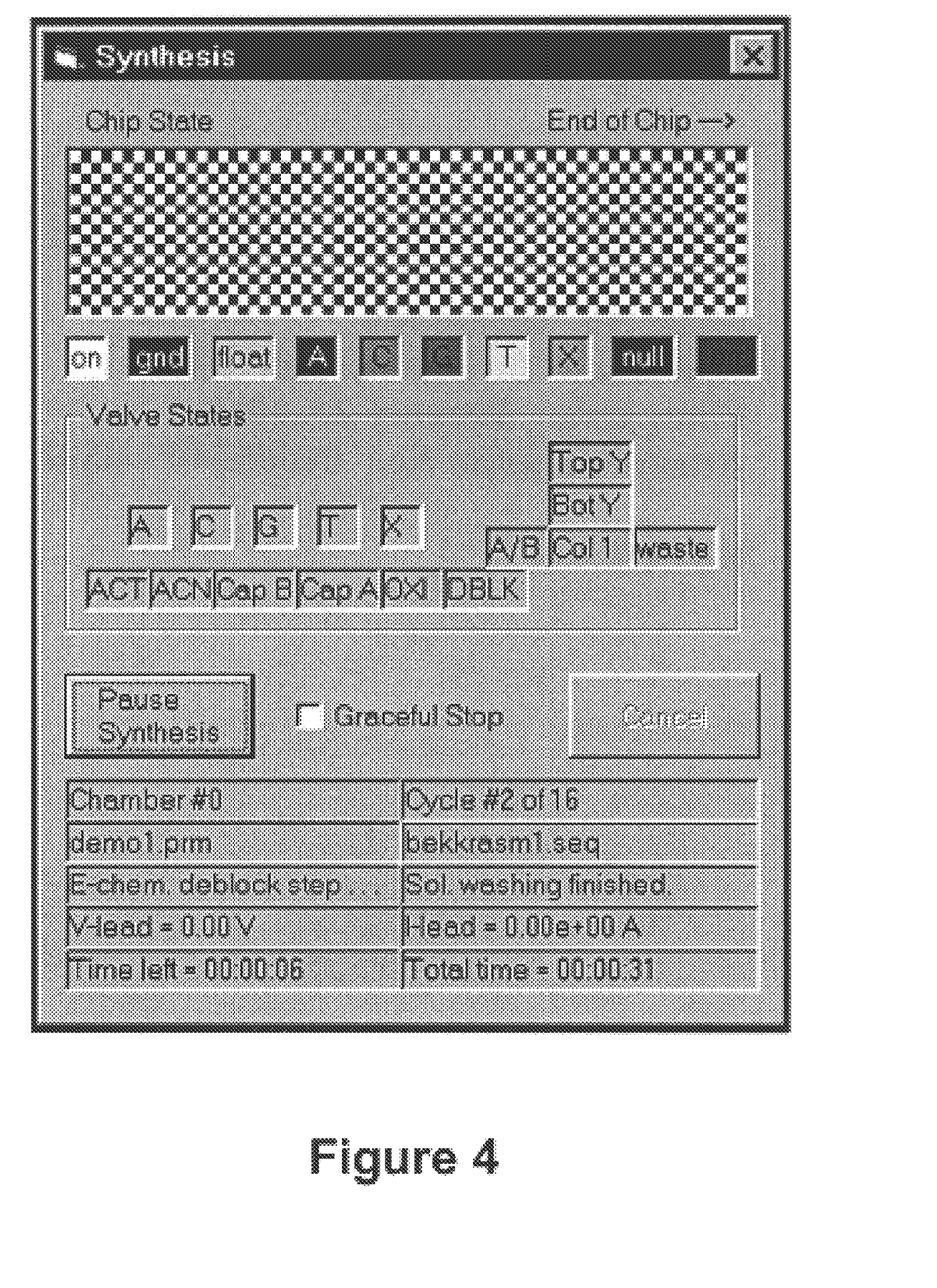

In FIG. 4, one can see what is displayed during DNA synthesis. Display features include the state of the chip (as represented in the graphical box labelled "chip state"), the state of valves in the synthesizer, display of the chamber number in which the DNA is being synthesized, the cycle number (the cycle of DNA synthesis the DNA synthesizer is on), the parameter file being used to set the parameters used in synthesis, the sequence being built, the chemical step the machine is on (in this case the "E-chem deblock step"), the subtask of that chemical step (in this case it is finished with the washing), the values that the voltage and current leads are set to, the time left in the synthesis, and the total time the synthesis is to run.

Figure 5:
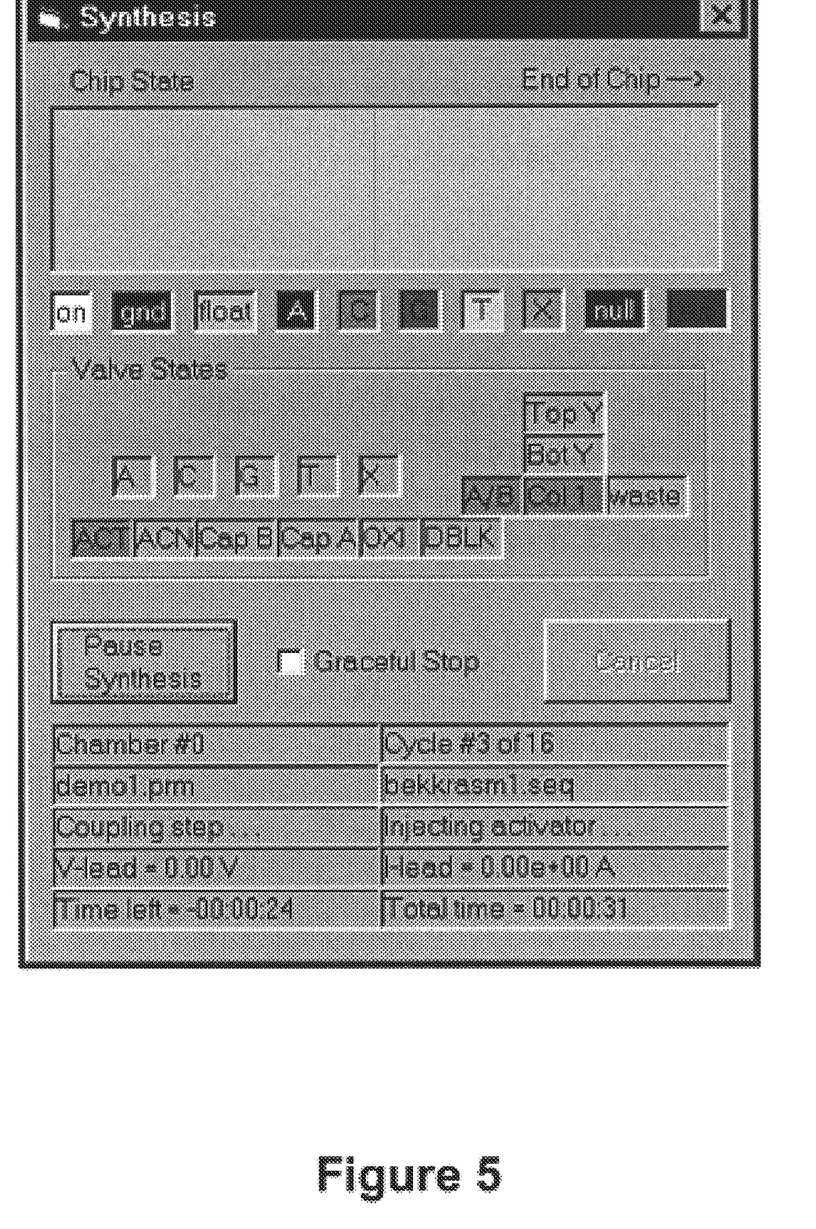
FIG. 5 demonstrates the same display during another part of the synthesis from a computer interface program designed according to the present invention, again displaying the state of the chip and various other features. Note that, in this stage, some of the valves are on as denoted by the green coloring. There are various ways that a user can interact with the processing equipment through the interface. There is a "pause synthesis" button for pausing the synthesis (say, if more reagents needed to be added or for some other reason), and there is a "graceful stop" box. When the "graceful stop" box is checked, the synthesis ends at the next full cycle but before the end of all cycles, allowing the operator to remove the chip before the end of the full synthesis but at a point where the DNA chain is complete up to that point.
Figure 6:
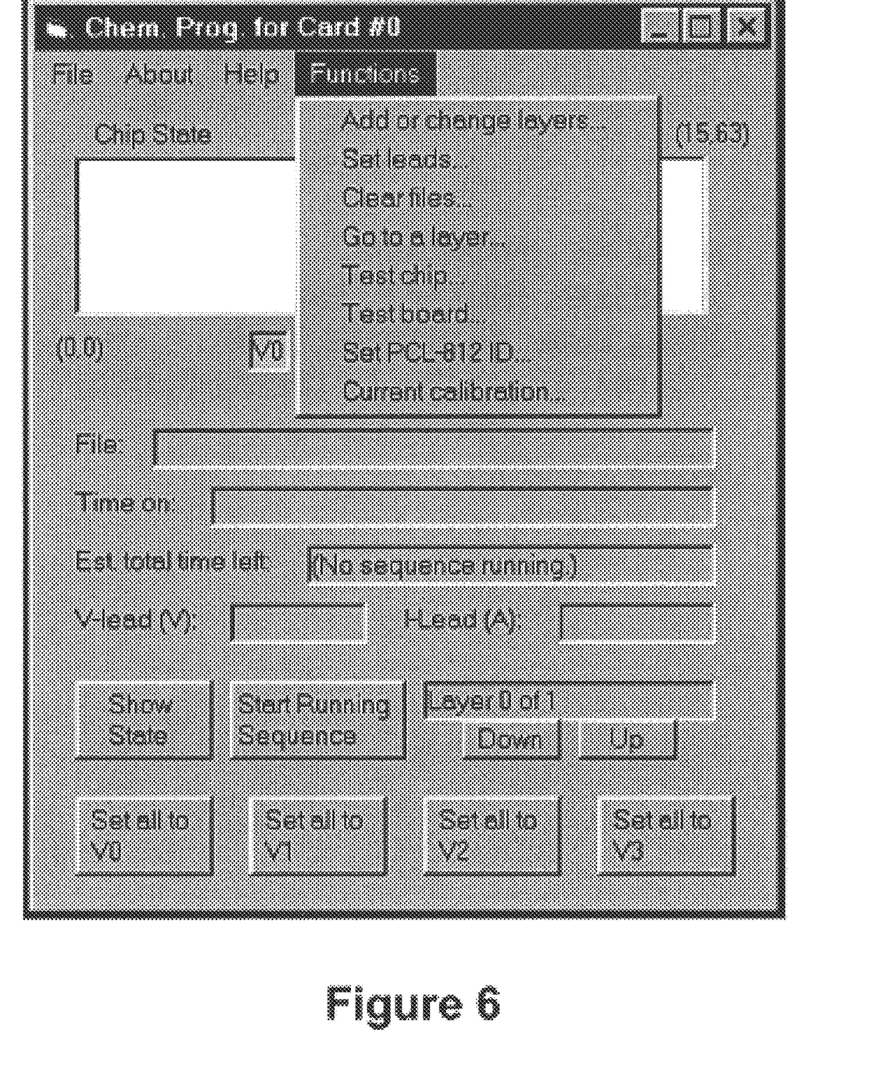
FIG. 6 demonstrates some of the various functions available in software from a computer interface program designed according to the present invention: adding layers to the sequence, setting voltage leads, clearing and displaying layers, testing the chip, testing the interface board, setting an ID number for another interface board, and calibrating the device that does electrical current measurement.

In FIG. 5, one can see the same display during another part of the synthesis, again displaying the state of the chip and the various other features. Note that, in this stage, some of the valves are on (as denoted by the green coloring). Also note that in FIGS. 3 and 4 there are various ways a user can interact with the processing equipment through the interface. There is a "pause synthesis" button for pausing the synthesis (say, if more reagents needed to be added or for some other reason), and there is a "graceful stop" box. When the "graceful stop" box is checked, the synthesis ends at the next full cycle but before the end of all cycles, allowing the operator to remove the chip before the end of the fall synthesis but at a point where the DNA chain is complete up to that point. Exemplary designs may be provided for electrochemistry and chip regulation. This setup is used for general manipulation of a chip, loading the chip with various patterns of voltages for various times, then loading another pattern, and so on. FIG. 6 shows various functions available in this software: adding layers to the sequence, setting voltage leads, clearing and displaying layers, testing the chip, testing the interface board, setting an ID number for another interface board, and calibrating the device that does electrical current measurement.

Figure 7:
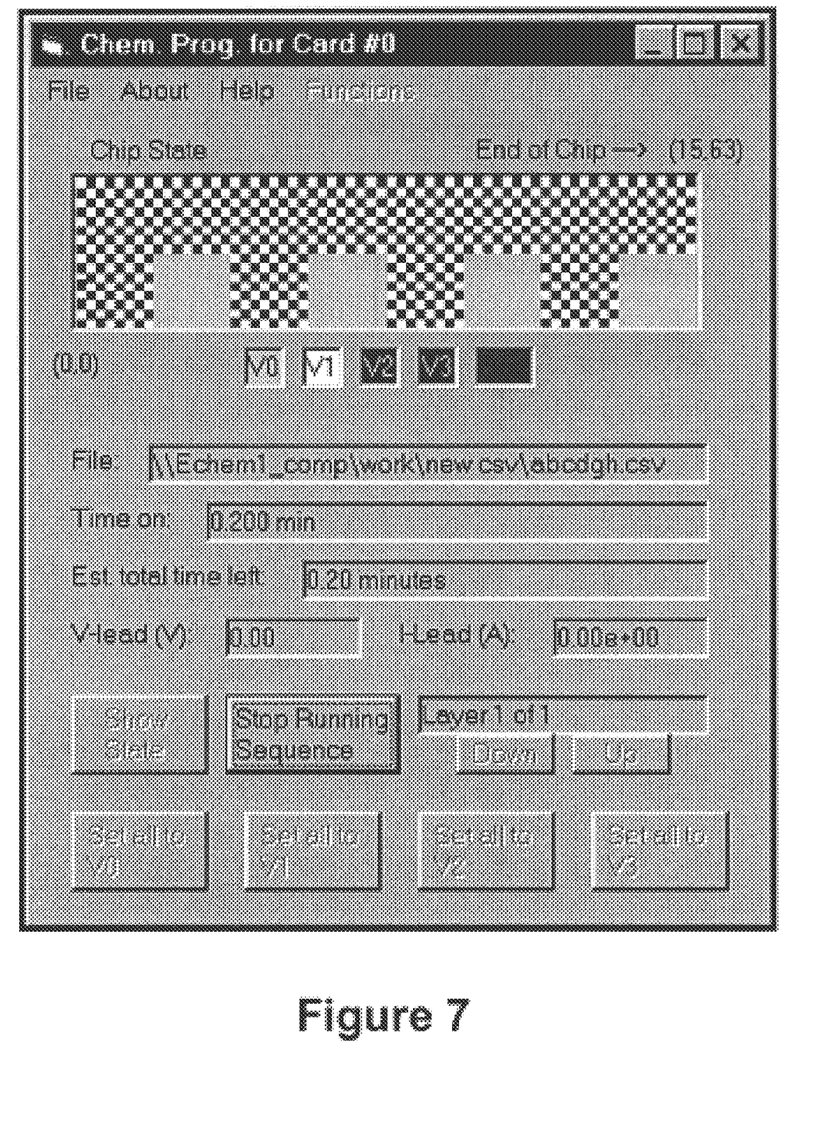
FIG. 7 demonstrates some of the display properties of the interface in operation from a computer interface program designed according to the present invention. The chip state is indicated showing what lines various electrodes are set to and what their states are. The layer in effect, how long that layer is to be on, the time left in the sequence, the voltage and current settings, etc. are also demonstrated.

FIG. 7 provides an example of the display properties of the interface in operation. Note that the chip state is indicated, showing what lines various electrodes are set to and what their states are. The layer in effect, how long that layer is to be on, the time left in the sequence, the voltage and current settings, etc. are also demonstrated. Note from FIGS. 6 and 7 that the user can stop running the sequence at any time. Such displays and interfaces need not be coupled directly to the processing equipment but could be connected to the processing equipment through a network, allowing the display and the processing equipment to be geographically separated. This is useful in the event where the processing equipment might need a special environment (say if it uses hazardous chemicals) or if the operator would like to interact with the equipment from his office or from another building or in another part of the world. It also allows more than one person to interact with the equipment at the same time. Hence, two or more people may see the status of parts of the process while it is running without being in the same location—they would need simply a display for each person, and two or more displays could interact with the same processing equipment.

The methods of the present invention are especially applicable to an electrochemical based solid or porous array. Such an array typically contains a plurality of electrode sites including an electrode and a driving member for delivering an electrical stimulus to the electrode. Moreover, a memory device is typically present at each electrode for receiving and storing a signal for delivering the electrical stimulus. The memory device typically controls the beginning, ending and magnitude of the electrical stimulus. Computer programs that may be easily designed by those skilled in the art according to the present invention may interface with each electrode site thereby allowing remote interface with the computer display. Such computer programs in accordance with the present invention allow the artisan to selectively provide current and voltage to the array thereby controlling the processing and synthesis of biological and chemical materials. Such programs effectively create an electronically controllable array that may be managed and monitored from a remote location.

One particularly preferred application of the present invention is in conjunction with the chemical synthesis arrays disclosed by Montgomery in WO 98/01221, the disclosure of which is herein incorporated by reference in its entirety. A diagrammatic representation of such an interface is provided in FIG. 2. In such a situation, it may be desirable for a user to determine whether a set of target nucleic acid sequences are in a solution. The target sequences may be transmitted from the user remotely via a network (such as the Internet) to a server. This server might then design capture probes to probe for the nucleic acid sequences of interest. The server then might then transmit the list of capture probes to a DNA-array synthesizer such as the ones described in WO 98/01221. The synthesizer is preferably remotely related from the server, and it then synthesizes the subject probes. Such synthesis is controlled by the internal server via programming that controls and/or monitors the array synthesizer. The set of probes synthesized thereby may then be used to determine whether the target nucleic acid sequences are present. In embodiments wherein the hybridization reaction to the target nucleic acid sequences is automated, the information resulting may be transmitted back to the user in a remote location via the internet or an intranet.

Although the invention has been described with reference to the presently preferred embodiments, it should be understood that various modifications can be made without departing from the spirit of the invention. Accordingly, the invention is limited only by the following claims.

What is claimed is:

1. A network infrastructure design to support custom DNA microarray synthesis and analysis system, comprising:

(a) a host server or servers having a software program capable of designing a set of probes to capture target sequences;

(b) a microarray synthesizer or a plurality of microarray synthesizers capable of synthesizing probes and communicating with the host server or servers over a LAN or Internet network;

(c) a hybridization unit capable of hybridizing and reading the DNA microarrays synthesized by the microarray synthesizer to obtain results of hybridization and communicating with the host server or servers to provide the results; and (d) a user interface or workstation communicating with the host server or servers and providing a list of target sequences to the host server or servers and to receive the results from the hybridization unit processed through the host server or servers.

* * * * *

(12) EX PARTE REEXAMINATION CERTIFICATE (7516th)
United States Patent
Anderson (10) Number: US 6,456,942 C1
(45) Certificate Issued: May 18, 2010

(54) NETWORK INFRASTRUCTURE FOR CUSTOM MICROARRAY SYNTHESIS AND ANALYSIS

(75) Inventor: Brooke P. Anderson, Millbrae, CA (US)

(73) Assignee: Combimatrix Corporation, Burlingame, CA (US)

Reexamination Request:
No. 90/008,469, Jan. 26, 2007

Reexamination Certificate for:
Patent No.: 6,456,942
Issued: Sep. 24, 2002
Appl. No.: 09/490,565
Filed: Jan. 25, 2000

Related U.S. Application Data
(60) Provisional application No. 60/116,954, filed on Jan. 25, 1998.

(51) Int. Cl.
*G06F 19/00* (2006.01)

(52) U.S. Cl. .................................. 702/19; 435/6; 436/8
(58) Field of Classification Search ........................ None
See application file for complete search history.

(56) References Cited

U.S. PATENT DOCUMENTS 5,795,716 A * 8/1998 Chee .............................. 435/6
6,408,308 B1 * 6/2002 Maslyn et al. ........... 707/104.1

OTHER PUBLICATIONS

DeRisi, J. et al., "Exploring the Metabolic and Genetic Control of Gene Expression on a Genomic Scale," *Science*, 1997, 278, 680–686.

Lashkari, D. et al., "Yeast microarrays for genome wide parallel genetic and gene expression analysis," *PNAS U.S.A.*, 1997, 94, 13057–13062.

* cited by examiner

*Primary Examiner*—Zoila E Cabrera (57) ABSTRACT

The present invention provides methods for interfacing computer technology with biological and chemical processing and synthesis equipment. In preferred embodiments, the present invention features methods for the computer to interface with equipment useful for biological and chemical processing and synthesis in a remote manner.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

* * * * *